United States Patent [19]

Mattock

[11] 4,250,008
[45] Feb. 10, 1981

[54] PURIFICATION OF FACTOR VIII

[75] Inventor: Patrick Mattock, Botley, England

[73] Assignee: United Kingdom Atomic Energy Authority, London, England

[21] Appl. No.: 112,633

[22] PCT Filed: Jun. 22, 1979

[86] PCT No.: PCT/GB 78/00038

§ 371 Date: Jun. 22, 1979

§ 102(e) Date: Jun. 22, 1979

[87] PCT Pub. No.: WO79/00299

PCT Pub. Date: May 31, 1979

[30] Foreign Application Priority Data

Nov. 17, 1977 [GB] United Kingdom ............... 47933/77

[51] Int. Cl.³ .................... G01N 27/26; A61K 35/14; A61K 35/16
[52] U.S. Cl. ........................ 204/180 R; 204/299 R; 23/230 B; 424/12
[58] Field of Search ........... 204/180 R, 180 S, 180 G, 204/180 P, 299, 301; 23/230 B; 424/12

[56] References Cited

U.S. PATENT DOCUMENTS

| | | | |
|---|---|---|---|
| 3,870,617 | 3/1975 | Bourat | 204/301 |
| 3,989,613 | 11/1976 | Gritzner | 204/301 X |
| 4,149,957 | 4/1979 | Gibson et al. | 204/301 |

FOREIGN PATENT DOCUMENTS 1431888  4/1976  United Kingdom .

OTHER PUBLICATIONS

Chem. Abstracts, vol. 54, No. 1, Jan. 10, 1960, col. 672(b).
Chem. Abstracts. vol. 52, No. 21, Nov. 10, 1958, col. 18751(g,h).

Primary Examiner—Arthur C. Prescott
Attorney, Agent, or Firm—Larson, Taylor and Hinds

[57] ABSTRACT

The invention is concerned with purification of Factor VIII containing solutions, such as blood plasma, by continuous flow electrophoresis.

Hitherto, purification of such solutions has been performed by methods such as cryoprecipitation which however have the disadvantages of poor recovery. In our invention, this problem is overcome by adjusting the pH of a Factor VIII containing solution to be in a range where the stability of Factor VIII is not adversely affected (e.g. 6 to 9) and then subjecting the solution to continuous flow electrophoresis to give purified Factor VIII fractions. If desired, the fractions may be further purified.

8 Claims, No Drawings

PURIFICATION OF FACTOR VIII

TECHNICAL FIELD

This invention relates to the purification of Factor VIII containing solutions, such as blood plasma, by continuous flow electrophoresis.

BACKGROUND ART

Factor VIII is the antihaemophilic factor in blood. Its actual structure is, at present, unknown though it is suspected to be a complex high molecular weight protein or possibly associated with such a protein. There is much interest in its extraction, e.g. from blood plasma, so that it can be used in the treatment of patients suffering from haemophilia. Factor VIII is, however, unstable and this has created difficulties in its extraction. Methods of extraction are, however, available such as a cryoprecipitation method. This method has the disadvantage of poor recovery (e.g. about 40%) of Factor VIII from the initial plasma and of giving rise to a dilute product, which accordingly creates problems of administration to the patient because of the large volume of product required to achieve suitable dose levels. The dilute product may, however, if required, be further purified and freeze dried to give a concentrated form of Factor VIII, but with further loss of Factor VIII activity.

DISCLOSURE OF INVENTION

We have now devised a method of extracting Factor VIII from blood plasma and other Factor VIII containing solutions, such as partly purified blood plasma, which, we believe, substantially overcomes the above-mentioned problems. Our method includes the application of continuous flow electrophoresis to Factor VIII extraction.

The present invention provides a method of purifying a Factor VIII containing aqueous solution characterised by the steps of (i) reducing the ionic strength of the solution to a level such that it is capable of being electrophoresed;

(ii) adjusting the pH of the solution to within a range where the stability of Factor VIII is not adversely affected;

(iii) subjecting the product of step (ii) to continuous flow electrophoresis by injecting the solution as a migrant solution into a second aqueous solution, laminarly flowing in an annular separation chamber as a carrier solution for the migrant solution and stabilised by means of an angular velocity gradient, and applying a constant electric field across the resulting mixture to produce a differential movement of the Factor VIII component of the migrant solution with respect to the other major components of the solution perpendicular to the direction of flow of the layer; and (iv) collecting the separated Factor VIII component.

If desired, the separated Factor VIII component, which is in aqueous solution, may be further purified, for example, by freeze drying, redissolving in water, adjusting the pH to 7 and removing insoluble material or preferably by concentrating using a hollow fibre concentrator before freeze drying. In specific examples, we have achieved an overall recovery of at least 60% from the initial plasma with a 14-fold purification over the initial plasma. Also, we have found that the final product contains virtually no fibrinogen, whilst the major contaminant is albumin which, we believe, however, may have little effect upon the Factor VIII.

Step (i) of our method has to be carried out in order to be able to carry out step (iii). A number of methods may be used in step (i) such as gel filtration and dialysis. We prefer to use dialysis because of its simplicity and because it causes no detectable loss of Factor VIII activity in Factor VIII containing solutions such as blood plasma.

The product of step (i) may in some cases require dilution before it can be used in subsequent steps (ii) and (iii) in order to lower the protein concentration to a level suitable for electrophoresis to be carried out.

Step (iii) is most conveniently carried out as generally described in U.K. Pat. No. 1,186,184 (corresponding to U.S. Pat. No. 3,616,453), which describes a process and apparatus where stabilisation of flowing streams in continuous flow electrophoresis is effected by an angular velocity gradient. Thus, in our method, the fractionation may be effected in an annular separation chamber defined between a central stationary cylinder (a stator) and an outer rotating cylinder (a rotor), which results in a gradient of angular velocity across the annular chamber giving laminar flow at high throughputs. The constant electric field is then applied across the annular chamber to produce the differential movement of the Factor VIII component of the migrant solution. Improvements and/or modifications of the apparatus described in U.K. Pat. No. 1,186,184 are described in U.K. Pat. Nos. 1,431,887 and 1,431,888 (corresponding to U.S. Pat. No. 3,844,926).

The pH of the migrant solution in step (iii) may suitably be in the range of 6 to 9 though we generally prefer that it is in the range of 7 to 8.5. The adjustment of the pH of the product of step (i) in step (ii) may suitably be carried out by means of an appropriate buffer solution. pH has to be adjusted as in step (ii) because of its effect on stability of Factor VIII. Thus, Factor VIII is stable at pH 7, but its stability decreases as the pH moves away from 7. However, if the residence time of the migrant solution under the conditions of step (iii) is short, it may be possible to carry out the step at pH's remote from 7. A further consideration is that, at pH's approaching 7, more electrical power is required to produce a given mobility of a component of the migrant solution because of its net charge and this may give rise to heating such as to affect the stability of the Factor VIII. Taking these conflicting requirements into account, we particularly prefer that the pH of the migrant solution is 7.5. A further preferment is that the electrical conductivity of the migrant solution is in the range of 0.75 to 1.0 mScm$^{-1}$ at 20° C.

Step (iv) may be carried out as described in U.K. Pat. Nos. 1,431,887 and 1,431,888. Thus, if our method is carried out as described in these specifications, the direction of migration of the migrant solution is centrifugal and the injection thereof accordingly effected at the inner side of the flow of the carrier solution. The direction of flow is generally upward and is helical in pattern because of the effect of the rotation of the rotor. Separated components may then be collected by means of an off-take system located in the stator and consisting of a series of parallel mazeplates with spacers. A particular separated component may then pass through one or more particular mazeplates and hence into collecting tube(s).

The invention also provides Factor VIII obtained by the present method.

BEST MODE FOR CARRYING OUT THE INVENTION

EXAMPLE 1

Fresh, frozen human blood plasma (250 ml) was thawed rapidly and dialysed overnight against an aqueous tris-citrate solution (10L; pH 7.0; conductivity 0.75 mScm$^{-1}$) at 4° C. in order to reduce the salt concentration of the plasma. The dialysed plasma was then diluted approximately 1.5 times with an aqueous tris-citrate solution to give a product of pH 7.5 and an electrical conductivity of 1.0 mScm$^{-1}$ at 20° C.

The above product, as a migrant solution, was then warmed to 20° C. and electrophoresed using a continuous electrophoretic separation apparatus of the type generally described in U.K. Pat. Nos. 1,431,887 and 1,431,888. The apparatus had 29 outlet ports, a stator radius of 40 mm, a rotor radius of 45 mm to give an annular gap of 5 mm, and electrodes 304 mm in length. A carrier solution at 2° C. comprising an aqueous tris-citrate solution (pH 7.5: electrical conductivity 0.75 mScm$^{-1}$ at 20° C.) was passed upwardly through the annular gap at a rate of 500 ml/minute and the flow stabilised by rotation of the rotor. The migrant solution was injected into the annular gap at a rate of 10 ml/minute. The electrophoresis was carried out at 35 amps and 27 volts giving a temperature rise of carrier solution of 20° C., i.e., from 2° C. to 22° C. The electrolytes were ammonium acetate (1 M, pH 7.5) for the cathode and an equal volume mixture (pH 7.5) of ammonium citrate (0.2 M) and ammonium phosphate (0.15 M) for the anode. Separated components containing Factor VIII activity as judged by a one-stage assay procedure were collected and those containing about 75% of the total Factor VIII clotting activity (which was from 4 to 5 of the outlets) were pooled together, freeze dried and stored at −25° C. The one-stage assay procedure used was as described in American Journal of Chemical Pathology, Vol. 61 No. 2 February 1974: "Reassessment of a Non-Haemophilic Reagent for Factor VIII (AHF) Determination" by de Angula & Frommel.

The above freeze dried product was redissolved in about 1/30th of the volume, from electrophoresis, of distilled water to give a concentration of about 15 mg/ml of protein, the pH adjusted to 7 using dilute ammonia solution and insoluble material removed by centrifugation at 15000 r.p.m. for 15 minutes. A further one-stage assay as above showed that about 80% of the Factor VIII activity of the pooled components had been recovered. Thus, the overall recovery from the initial plasma was at least 60%, with a 14-fold purification over the initial plasma in relation to protein concentration.

The final product contained virtually no fibrinogen; the major contaminant was albumin. Factor VIII related antigen was also present; the ratio of clotting activity to antigen was approximately the same as in the initial plasma (The antigen is the protein associated with the Factor VIII clotting activity).

EXAMPLE 2

The procedure of Example 1 was repeated with the exception that, before freeze drying was carried out, the collected Factor VIII containing components were concentrated 10 to 20 fold using a hollow fibre concentrator (from Amicon Corporation) with a 10,000 molecular weight cut off. The resulting concentrate was then dialysed at 4° C. against 0.025 M Tris acetate of pH 7.5 for at least two hours before freeze drying.

The product, on redissolving in about 1/30th of the volume, from electrophoresis, of distilled water, was stable for 3 to 4 days at 4° C.; also, recovery of Factor VIII activity was found to be more reproducible than by using the procedure of Example 1.

I claim:

1. A method of purifying a Factor VIII containing aqueous solution characterised by the steps of
   (i) reducing the ionic strength of the solution to a level such that it is capable of being electrophoresed;
   (ii) adjusting the pH of the solution to within a range where the stability of Factor VIII is not adversely affected;
   (iii) subjecting the product of step (ii) to continuous flow electrophoresis by injecting the solution, as a migrant solution, into a second aqueous solution, laminarly flowing in an annular separation chamber as a carrier solution for the migrant solution and stabilised by means of an angular velocity gradient, and applying a constant electric field across the resulting mixture to produce a differential movement of the Factor VIII component of the migrant solution with respect to the other major components of the solution perpendicular to the direction of flow of the layer; and
   (iv) collecting the separated Factor VIII component.

2. A method according to claim 1 wherein the pH of the solution in step (ii) is adjusted to be in the range of 6 to 9.

3. A method according to claim 2 wherein the range is 7 to 8.5.

4. A method according to claim 3 wherein the pH is 7.5.

5. A method according to any of the preceding claims wherein the electrical conductivity of the solution in step (ii) is adjusted to be in the range of 0.75 to 1.0 mScm$^{-1}$ at 20° C.

6. A method according to claim 1 wherein the separated Factor VIII component is further purified.

7. A method according to claim 6 wherein the further purification is effected by concentration using a hollow fibre concentrator followed by freeze drying.

8. Factor VIII prepared by a method according to claim 1.

* * * * *